(12) United States Patent
Lezdey et al.

(10) Patent No.: US 7,270,979 B1
(45) Date of Patent: Sep. 18, 2007

(54) DNA FOR EXPRESSION OF ALPHA 1-ANTITRYPSIN IN METHYLOTROPIC YEAST

(75) Inventors: John Lezdey, Indian Rocks Beach, FL (US); K. Anne Kronis, Tampa, FL (US); Darren Lezdey, Indian Rocks Beach, FL (US)

(73) Assignee: Alphamed Pharmaceuticals Corp, Largo, FL (US)

( * ) Notice: Subject to any disclaimer, the term of this patent is extended or adjusted under 35 U.S.C. 154(b) by 595 days.

(21) Appl. No.: 10/672,177

(22) Filed: Sep. 26, 2003

Related U.S. Application Data

(63) Continuation-in-part of application No. 09/981,073, filed on Oct. 16, 2001, now abandoned, which is a continuation-in-part of application No. 09/526,401, filed on Mar. 15, 2000, now abandoned.

(51) Int. Cl.
*C12N 15/09* (2006.01)
*C12P 21/02* (2006.01)
(52) U.S. Cl. ...................................... 435/69.2; 435/69.9
(58) Field of Classification Search .................... None
See application file for complete search history.

*Primary Examiner*—Nancy Vogel
(74) *Attorney, Agent, or Firm*—John Lezdey

(57) ABSTRACT

Alpha 1-antitrypsin is prepared by growing in a fermentor methylotropic yeast transformants containing in their genome at least one copy of DNA encoding alpha 1-antitrypsin, in operational linkage with DNA encoding a signal sequence, which is effective for directing secretion of proteins from the host cells, DNA constructs and recombinant yeast strains used for the expression and secretion of alpha 1-antritrypsin are also provided. The fermentation medium requires a pH of 6.5 to 7.5. The fermentation is at a pH between 5 and 6.8.

4 Claims, 2 Drawing Sheets

SEQUENCE LISTING (1) GENERAL INFORMATION:

(iii) NUMBER OF SEQUENCES: 8

(2) INFORMATION FOR SEQ ID NO: 1

(i) SEQUENCE CHARACTERISTICS:
      (A) LENGTH: 32
      (B) TYPE: NUCLEIC ACID
      (C) STRANDEDNESS: SINGLE
      (D) TOPOLOGY: UNKNOWN (ii) MOLECULE TYPE: DNA   (Genomic DNA)

(iii) HYPOTHETICAL: No (iv) ANTI-SENSE: No (vi) ORIGINAL SOURCE:

-continued (A) ORGANISM: HUMAN (ix) FEATURE:
        (C) IDENTIFICATION METHOD: gene scan (xi) SEQUENCE DESCRIPTION: SEQ ID NO: 1:

CTC GAG AAG AGA GAG GAT CCC CAG GGA GAT GC                                      32

(2) INFORMATION FOR SEQ ID NO: 2:

(i) SEQUENCE CHARACTERISTICS:
        (A) LENGTH: 32
        (B) TYPE: NUCLEIC ACID
        (C) STRANDEDNESS: SINGLE
        (D) TOPOLOGY: UNKNOWN (ii) MOLECULE TYPE: DNA  (Genomic DNA)

(iii) HYPOTHETICAL: No (iv) ANTI-SENSE: No (vi) ORIGINAL SOURCE:
        (A) ORGANISM: HUMAN (ix) FEATURE:
        (C) IDENTIFICATION METHOD: gene scan (xi) SEQUENCE DESCRIPTION: SEQ ID NO: 2:

GC GGC CGC TTA TTT TTG GGT GGG ATT CAG CAG                                      32

(2) INFORMATION FOR SEQ ID NO: 3

(i) SEQUENCE CHARACTERISTICS:
        (A) LENGTH: 24
        (B) TYPE: NUCLEIC ACID
        (C) STRANDEDNESS: SINGLE
        (D) TOPOLOGY: UNKOWN (ii) MOLECULE TYPE: DNA  (Genomic DNA)

(iii) HYPOTHETICAL: No (iv) ANTI-SENSE: No (vi) ORIGINAL SOURCE:
        (A) ORGANISM: HUMAN (ix) FEATURE:
        (C) IDENTIFICATION METHOD: gene scan (xi) SEQUENCE DESCRIPTION: SEQ ID NO: 3:

CAG AAG ACA GAT ACA TCC CAC CAT                                                 24

(2) INFORMATION FOR SEQ ID NO: 4:

(i) SEQUENCE CHARACTERISTICS:
        (A) LENGTH: 22
        (B) TYPE: NUCLEIC ACID
        (C) STRANDEDNESS: SINGLE
        (D) TOPOLOGY: UNKNOWN (ii) MOLECULE TYPE: DNA  (Genomic DNA)

(iii) HYPOTHETICAL: No (iv) ANTI-SENSE: No (vi) ORIGINAL SOURCE:
        (A) ORGANISM: HUMAN (ix) FEATURE:
        (C) IDENTIFICATION METHOD: gene scan

```
        (xi) SEQUENCE DESCRIPTION: SEQ ID NO: 4:

AGG ATT TCA TCG TGA GTG TCA G                                           22

(2) INFORMATION FOR SEQ ID NO: 5:

(i) SEQUENCE CHARACTERISTICS:
         (A) LENGTH: 24
         (B) TYPE: NUCLEIC ACID
         (C) STRANDEDNESS: SINGLE
         (D) TOPOLOGY: UNKNOWN (ii) MOLECULE TYPE: DNA  (Genomic DNA)

(iii) HYPOTHETICAL: No (iv) ANTI-SENSE: No (vi) ORIGINAL SOURCE:
         (A) ORGANISM: HUMAN (ix) FEATURE:
         (C) IDENTIFICATION METHOD: gene scan (xi) SEQUENCE DESCRIPTION: SEQ ID NO: 5:

TAC TCA AGG GAA AAT TGT GGA TTT                                         24

(2) INFORMATION FOR SEQ ID NO: 6:

(i) SEQUENCE CHARACTERISTICS:
         (A) LENGTH: 24
         (B) TYPE: NUCLEIC ACID
         (C) STRANDEDNESS: SINGLE
         (D) TOPOLOGY: UNKNOWN (ii) MOLECULE TYPE: DNA  (Genomic DNA)

(iii) HYPOTHETICAL: No (iv) ANTI-SENSE: No (vi) ORIGINAL SOURCE:
         (A) ORGANISM: HUMAN (ix) FEATURE:
         (C) IDENTIFICATION METHOD: gene scan (xi) SEQUENCE DESCRIPTION: SEQ ID NO: 6:

AGC TTC TTA CAG TGC TGG ATG TTA                                         24

(2) INFORMATION FOR SEQ ID NO: 7:

(i) SEQUENCE CHARACTERISTICS:
         (A) LENGTH: 24
         (B) TYPE: NUCLEIC ACID
         (C) STRANDEDNESS: SINGLE
         (D) TOPOLOGY: UNKNOWN (ii) MOLECULE TYPE: DNA  (Genomic DNA)

(iii) HYPOTHETICAL: No (iv) ANTI-SENSE: No (vi) ORIGINAL SOURCE:
         (A) ORGANISM: HUMAN (ix) FEATURE:
         (C) IDENTIFICATION METHOD: gene scan (xi) SEQUENCE DESCRIPTION: SEQ ID NO: 7:

GTT CAA CAA ACC CTT TGT CTT CTT                                         24
```

(2) INFORMATION FOR SEQ ID NO: 8:

(i) SEQUENCE CHARACTERISTICS:
        (A) LENGTH: 24
        (B) TYPE: NUCLEIC ACID
        (C) STRANDEDNESS: SINGLE
        (D) TOPOLOGY: UNKNOWN (ii) MOLECULE TYPE: DNA  (Genomic DNA)

(iii) HYPOTHETICAL: No (iv) ANTI-SENSE: No (vi) ORIGINAL SOURCE:
        (A) ORGANISM: HUMAN (ix) FEATURE:
        (C) IDENTIFICATION METHOD: gene scan (xi) SEQUENCE DESCRIPTION: SEQ ID NO: 8:

GGG AGA CTT GGT ATT TTG TTC AAT        24

DNA FOR EXPRESSION OF ALPHA 1-ANTITRYPSIN IN METHYLOTROPIC YEAST

This application is a continuation-in-part of application Ser. No. 09/981,073 filed Oct. 16, 2001, now abandoned which is a continuation-in-part of application Ser. No. 09/526,401 filed Mar. 15, 2000, now abandoned.

FIELD OF THE INVENTION

The invention relates to a process of recombinant DNA technology for producing glycosylated alpha 1-antitrypsin (AAT) peptides in methylotropic yeast such as *Pichia pastoris*. The invention further relates to the methylotrophic yeast transformants, DNA fragments and expression vectors used for their production and cultures contained therein.

BACKGROUND OF THE INVENTION

Alpha 1-antitrypsin is a protease inhibitor present in mammalian blood whose apparently major physiological function is to inhibit elastase, a potent protease which hydrolyzes structural proteins. Alpha 1-antitrypsin also inhibits other serine proteases. The normal plasma level of alpha 1-antitrypsin is about 2 mg/ml. A low level of alpha-1-antitrypsin in the blood may be associated with chronic obstructive pulmonary emphysema and infantile liver cirrhosis. Under many inflammatory conditions, an acute-phase response is initiated and the concentration of alpha-1-antitripsin is substantially increased. In order to study and treat alpha-1-antitrypsin deficiency and to be involved in the mechanism of the acute-phase response, it is therefore desirable to have a pure alpha-1-antitrypsin protein. In particular, it is desirable to have a source of antitrypsin protein produced by microorganisms through genetic engineering techniques.

The sequencing of chromosomal DNA coding for alpha antitrypsin has been described by Kurachi et al., *Proc. Natl. Acad. Sci. U.S.A.*, 78, 6826-6830 (1981) and by Chandra et al., *Biochem. Biophys. Res. Comm.*, 103, 751-758 (1981), the disclosures of which are incorporated herein by reference.

U.S. Pat. Nos. 4,839,282 and 5,218,091 which are incorporated herein by reference, discloses a process for expressing human non-glycosylated alpha 1-antitrypsin in *Saccharomyces cerevisiae* (Bakers yeast) which is difficult to upscale.

To overcome the major problems associated with the expression of recombinant gene products in *S. cerevisiae* (e.g., loss of selection for plasmid maintenance and problems concerning plasmid distribution, copy number and stability in fermentors operated at high cell density), a yeast expression system based on methylotrophic yeast, such as for example, *Pichia pastoris*, has been developed. A key feature of this unique system lies with the promoter employed to drive heterologous gene expression. This promoter, which is derived from a methanol-responsive gene of a methylotrophic yeast, is frequently highly expressed and tightly regulated (see, e.g., European Patent Application No. 85113737.2, published Jun. 4, 1976, under No. 0 183 071 and issued in the U.S. on Aug. 8, 1989, as U.S. Pat. No. 4,855,231). Another key feature of expression systems based on methylotrophic yeast is the ability of expression cassettes to stably integrate into the genome of the methylotrophic yeast host, thus significantly decreasing the chance of vector loss.

Although the methylotrophic yeast *P. pastoris* has been used successfully for the production of various [Cregg et al., *Bio/Technology* 5, 479 (1987)], lysozyme and invertase [Digan et al., *Developments in Industrial Microbiology* 29, 59 (1988); Tschopp et al., *Bio/Technology* 5, 1305 (1987)], endeavors to produce other glycosylated heterologous gene products in *Pichia*, especially by secretion, have given mixed results. At the present level of understanding of methylotrophic yeast expression systems, it is unpredictable whether a given gene can be expressed to an appreciable level in such yeast of whether the yeast host will tolerate the presence of the recombinant gene product in its cells. In addition, it is unpredictable whether desired or undesired proteolysis of the primary product will occur, and if the resulting proteolytic products are biologically active. Further, it is especially difficult to foresee if a particular protein will be secreted by the methylotrophic yeast host, and if it is, at what efficiency. Even for the non-methylotrophic yeast *S. cerevisiae*, which has been considerably more extensively studied than *P. pastoris*, the mechanism of protein secretion is not well defined and understood.

U.S. Pat. No. 5,612,198 to Brierley et al, which is herein incorporated by reference, discloses the production of insulin-like growth factor-1 in methylotrophic yeast.

SUMMARY OF THE INVENTION

Expression systems and methods using the expression systems for the production of biologically active alpha 1-antitrypsin (AAT) using methylotrophic yeast host cells are provided. The methods of production are readily scaled up from shake-flask cultures to large scale fermentors with no loss in AAT productivity and without the need for making major changes in the fermentation conditions used for the growth of the transformed strains. Methods for isolation and purification of the AAT product are also provided.

The expression systems and methods provided herein avoid the problems encountered with heterologous protein expression in *S. cerevisiae* in which high level expression can only be achieved by the introduction of multicopy plasmids into the host cells.

The expression system described herein uses methylotrophic yeast host cells, such as for example, *P. pastoris* for the expression of AAT. Key features of the system include the ability to stably integrate and express multiple copies of the DNA encoding AAT and the DNA encoding the signals that direct secretion and processing of the AAT and the ability to properly process mature AAT from the expressed precursor form of AAT and to secrete the resulting mature glycosylated AAT product.

Another feature of the system resides in selection of the promoter that has been used to control expression of the DNA encoding AAT. The promoter, which is derived from a methanol-responsive gene, such as AOX1, of a methylotrophic yeast, is tightly regulated and provides for high-level regulated expression of genes placed under its control.

Expression and secretion of high levels of glycosylated AAT peptide has been accomplished by transforming a methylotrophic yeast host with a DNA construct that contains at least one copy, but may contain as many as six or more copies, of DNA encoding an AAT peptide in which the DNA is operably linked with DNA encoding a signal sequence that is effective for directing the processing and secretion of the AAT peptide product. The DNA construct also includes a promoter region, which directs expression of the DNA encoding the signal sequence and AAT peptide, and a transcription terminator functional in a methylotrophic yeast.

The DNA construct provided here also includes sequences of nucleotides that have sufficient homology with a target gene in the methylotrophic yeast host cell genome to effect stable integration. Integration takes place by addition or replacement at the site of the target gene. Alternatively, the DNA construct is provided as part of a circular plasmid that integrates by addition at a site of homology between the host and the plasmid.

In accordance with other embodiments, expression vectors containing the DNA construct, which includes at least one copy of an expression cassette, are provided.

According to a still further embodiment of the present invention, there is provided a process for producing AAT peptides by growing methylotrophic yeast transformants containing in their genome at least one copy of a DNA sequence operably encoding an AAT peptide, operably associated with DNA encoding the *S. cerevisiae* AMF pre-pro sequence both under the regulation of a promoter region of a methanol responsive gene of a methylotrophic yeast, under condition allowing the expression of said DNA sequence in said transformants and secreting AAT peptides into the culture medium. Cultures of viable methylotrophic yeast cells capable of producing AAT peptides are also within the scope of the present invention.

The polypeptide product produced in accordance with the present invention is secreted to the culture medium at surprisingly high concentrations; the level of AAT peptides secretion is higher than the *S. cerevisiae* results published in the literature. In addition to the unique properties of the invention expression system, the excellent results obtained in the practice of the present invention are also due to the fact that the *S. cerevisiae* alpha-mating factor pre-pro sequence functions unexpectedly well to direct secretion of AAT peptides in methylotrophic yeast.

Yeast species contemplated for use in the practice of the present invention are methylotrophs, i.e., species which are able to grow on methanol (as well as other) carbon source nutriment. Species which have the biochemical pathways necessary for methanol utilization fall into four genera, i.e., *Candida, Hansenula, Pichia*, and *Torulopsis*. Of these, a substantial amount is known about the molecular biology of members of the species *Hansenula polymorpha* and *Pichia pastoris*.

The presently preferred yeast species for use in the practice of the present invention is *Pichia pastoris*. The *Pichia* strains include X33, GS115, KM71 and SMD1168H. The fermentation is essentially performed at a pH between 5 and 6.8.

DESCRIPTION OF THE PREFERRED EMBODIMENTS

Figure 1:
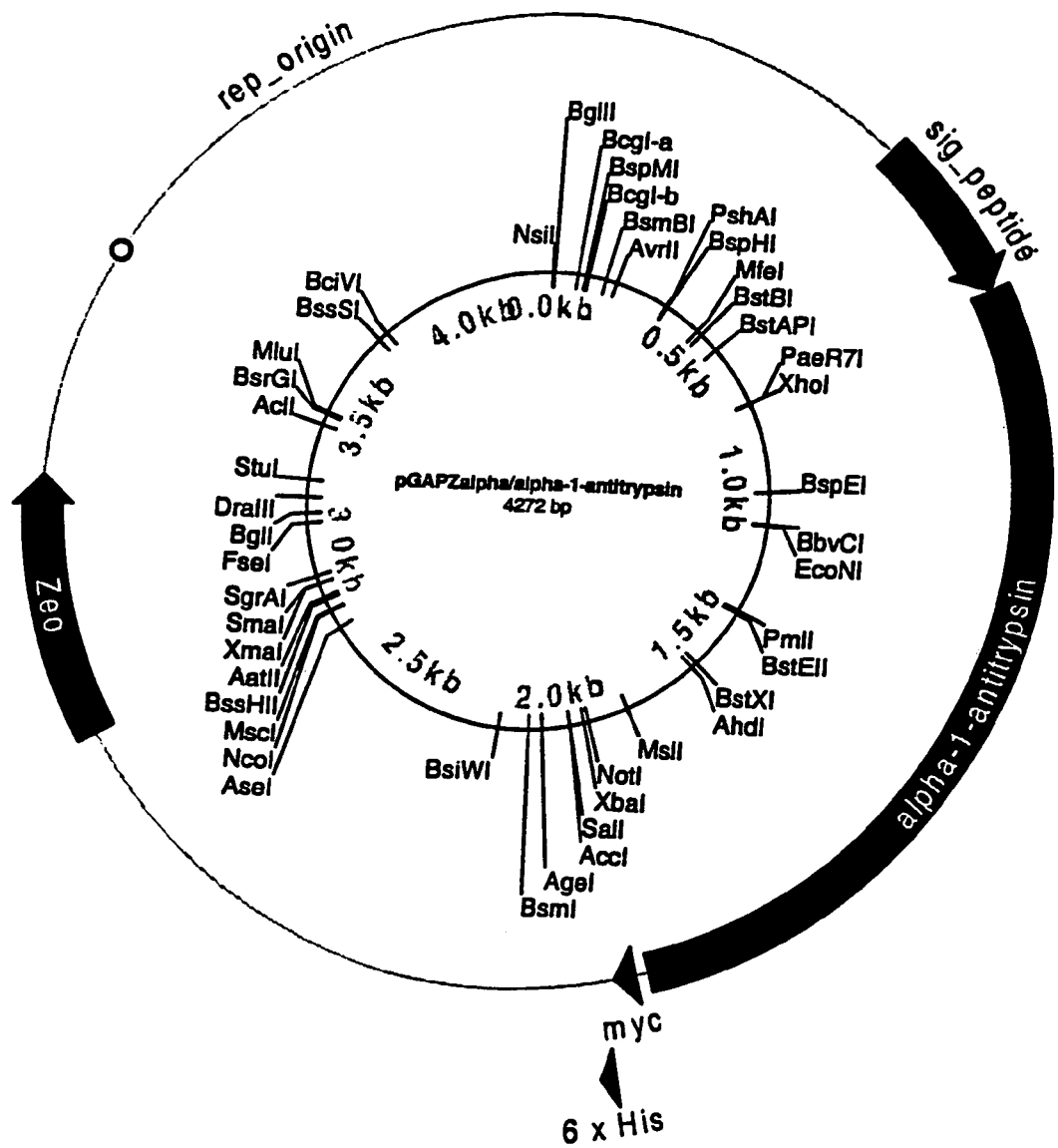
FIG. 1 is a schematic representation of expression vestor pGAPZ alpha/alpha1-antitrypsin used in the invention.
Figure 2:
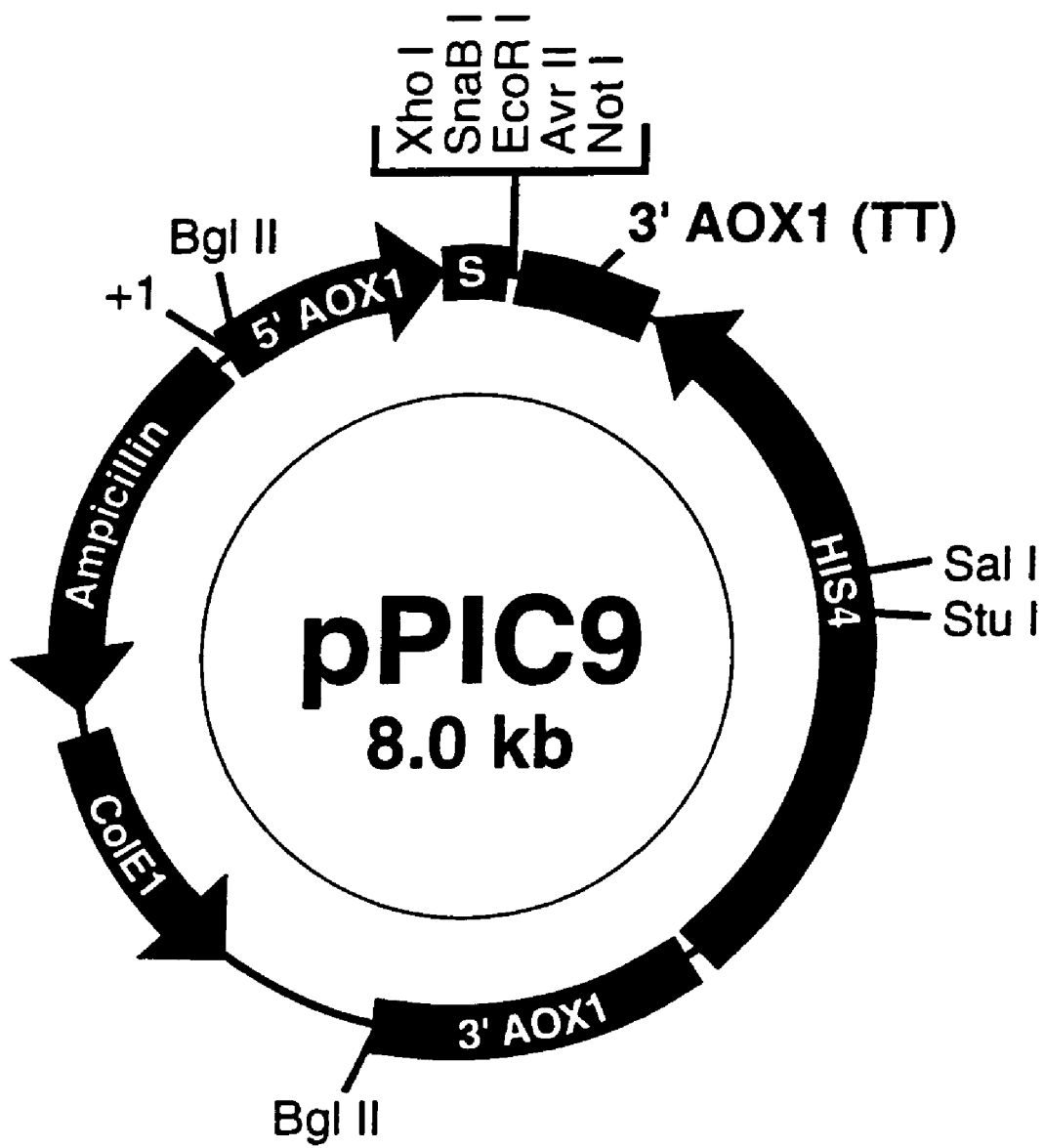
FIG. 2 illustrates a plasmid used in the present invention.

According to the present invention there is prepared Alpha 1-antitrypsin (AAT), a naturally occurring polypeptide by growing methylotrophic yeast tranformants containing in their genome at least one copy of DNA encoding AAT in operational linkage with DNA encoding sequence, which is effective for secretion of proteins from host cells. As used herein, AAT or an AAT peptide is intended to include all the glycosylated alleic variations of AAT. Moreover, derivatives obtained by simple modification of amino acid sequence of the naturally occurring product, such as by way of site-directed mutagenesis or other standard procedures are included within the scope of the present invention. Forms of AAT including hyperglycosylated AAT that exhibit similar biological activity to naturally occurring AAT are also encompassed by the present invention. It is intended that the AAT peptide, as used herein, includes any peptide that has the ability to bind to AAT receptors and that exhibits the ability to form a complex with elastase in a standard activity assay which is known in the art.

As used herein, expression cassette refers to a DNA construct that includes sequences functional for both the expression and the secretion of AAT. Accordingly, an expression cassette includes DNA encoding a promoter region, DNA encoding a transcription terminator region, and sequences sufficient for translation, secretion and proper processing of the expressed peptide. In addition, in preferred embodiments, the expression cassette is on a fragment that includes sequences at 5' and 3' ends that are homologous to introduction into the host cell; the expression cassette is stably integrated into the host cell genome.

As used herein, the term DNA construct embraces expression cassettes and also includes DNA fragments that include more than one expression cassette.

As used herein, the term operative linkage or operably associated refers to the relationship among elements of a DNA construct in which the elements are arranged whereby regulatory sequences of nucleotides that are part of the construct directly or indirectly control expression of the DNA in the construct, including DNA encoding a protein or a peptide.

As used herein, the term "a DNA fragment operably encoding AAT peptides" includes DNA fragments encoding AAT or any other "AAT peptide" as defined herein-above. DNA encoding AAT is known in the art and may be obtained by chemical synthesis or by transcription of messenger RNA (mRNA) corresponding to AAT into complementary DNA (cDNA) and converting the latter into a double stranded cDNA. Chemical synthesis of a gene for human AAT. The requisite DNA sequence can also be removed, for example, by restriction enzyme digestion of known vectors harboring the AAT gene. Examples of such vectors and the means for their preparation are well known to those of skill in the art. See, e.g., Niwa et al. (1986) *Annals of the NY Academy of Science*, 469: 31-52, and Buell et al. (1985) *Nucleic Acids Research*, 13: 1923-1938.

As used herein, the term expression vector is intended to include vectors capable of expressing DNA that are in operational association with other sequences capable of effecting their expression, such as promoter sequences, in a selected host cell. In general, expression vectors usually used in recombinant DNA technology are often in the form of "plasmids" which are circular, double-stranded DNA loops, extrachromosomal elements.

As used herein, the terms "vector" and "plasmid" are used interchangeably and are not intended to be limited, but to include any expression vectors or means that permit heterologous DNA to be expressed in a particular host cell.

As used herein, the term "culture" means a propagation of cells in a medium conducive to their growth, and all subcultures thereof. The term "subculture" refers to a culture of cells grown from cells of another culture (source culture), or any subculture of the source culture, regardless of the number of times subculturing has been performed between the subculture of interest and the source culture.

The amino acids that occur in the various sequences of amino acid set forth in the specification have their usual, three-and one-letter abbreviations, routinely used in the art:

| Amino Acid | Abbreviation | |
|---|---|---|
| L-Alanine | Ala | A |
| L-Arginine | Arg | R |
| L-Asparagine | Asn | N |
| L-Aspartic acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

Host Cells.

Yeast species contemplated for Use herein are methylotrophic yeast that are able to grow on methanol as a carbon source. Species intended for use herein have the biochemical pathways necessary for methanol utilization and fall into four genera, *Candida, Hansenula, Pichia*, and *Torulopsis*. A substantial amount is known about the molecular biology of members of the species *Hansenula polymorpha* and *Pichia Pastoris*.

*P. pastoris* is the presently preferred yeast species. *P. pastoris* is a known industrial yeast strain that is capable of efficiently utilizing methanol as the sole carbon and energy source.

There are a number of methanol responsive genes in methylotrophic yeast, the expression of each being controlled by methanol responsive regulatory regions (also referred to as promoters). Any of such methanol responsive promoters are suitable for use in the practice of the present invention. Examples of specific regulatory regions include the promoter for the primary alcohol oxidase gene from *Pichia pastoris* AOX1.

The presently preferred promoter region employed to drive AAT gene expression is derived from a methanol-regulated alcohol oxidase gene of *P. pastoris*. The AOX1 gene, including its promoter, has been isolated and thoroughly characterized; see Ellis et al., *Mol. Cell. Biol.* 5, 1111 (1985) and U.S. Pat. No. 4,855,231.

The expression cassette used for transforming methylotrophic yeast cells contains, in addition to a methanol responsive promoter of a methylotrophic yeast gene and the AAT encoding DNA sequence, a DNA sequence encoding the in-reading frame *S. cerevisiae* AMG pre-pro sequence.

The transcription terminator functional in a methylotrophic yeast used in accordance with the present invention has either (a) a subsegment which encodes a polyadenylation signal and polyadenylation site in the transcript, and/or (b) a subsegment which provides a transcription termination signal for transcription from the promoter used in the expression cassette. The term "expression cassette" as used herein, and throughout the specification and claims, refers to a DNA sequence, which includes sequences functional for both the expression and the secretion processes. The entire transcription terminator is taken from a protein-encoding gene, which may be the same or different from the gene which is the source of the promoter.

For the practice of the present invention it is preferred that multiple copies of the above-described expression cassettes be contained on one DNA fragment, preferably in a head-to-tail orientation.

The DNA fragments according to the invention optionally further comprise a selectable marker gene. For this purpose, any selectable marker gene functional in methylotrophic yeast may be employed, i.e., any gene which confers a phenotype upon methylotrophic yeast cells, thereby allowing them to be identified and selectively grown from among a vast majority of untransformed cells. Suitable selectable marker genes include, for example, selectable marker systems composed of an auxotrophic mutant *P. pastoris* host strain and a wild type biosynthetic genes which complements the host's defect.

If the yeast host is transformed with a linear DNA fragment containing the AAT gene under the regulation of a promoter region of a *P. pastoris* gene and AMF sequences necessary for processing and secretion, the expression cassette is integrated into the host genome by any of the gene replacement techniques known in the art, such as by one-step gene replacement [see e.g., Rothstein, *Methods Enzymol.* 101, 202 (1983); Cregg et al., *Bio/Technology* 5, 479 (1987); and U.S. Pat. No. 4,882,279] or by two-step qene replacement methods [see e.g., Scherer and Davis, *Proc. Natl. Acad. Sci.* U.S.A., 76, 4951 (1979)]. The linear DNA fragment is directed to the desired locus, i.e., to the target gene to be disrupted, by means of flanking DNA sequences having sufficient homology with the target gene to effect integration of the DNA fragment therein. One-step gene disruptions are usually successful if the DNA to be introduced has as little as 0.2 kb homology with the fragment locus of the target gene; it is however, preferable to maximize the degree of homology for efficiency.

In the DNA fragments of the present invention, the segments of the expression cassette(s) are said to be "operationally associated" with one another. The DNA sequence encoding AAT peptides is positioned and oriented functionally with respect to the promoter, the DNA sequence encoding the *S. cerevisiae* AMF pre-pro sequence, and the transcription terminator. Thus, the polypeptide encoding segment is transcribed under regulation of the promoter region, into a transcript capable of providing, upon translation, the desired polypeptide. Because of the presence of the AMF pre-pro sequence, the expressed AAT product is found as a secreted entity in the culture medium. Appropriate reading frame positioning and orientation of the various segments of the expression cassette are within the knowledge of persons of ordinary skill in the art; further details are given in the Examples.

The DNA fragment provided by the present invention may include sequences allowing for its replication and selection in bacteria, especially *E. coli*. In this way, large quantities of the DNA fragment can be produced by replication in bacteria.

Methods of transforming methylotrophic yeast, such as, for example, *Pichia pastoris*, as well as methods applicable for culturing methylotrophic yeast cells containing in their genome a gene encoding a heterologous protein, are known generally in the art.

According to the invention, the expression cassettes are transformed into methylotrophic yeast cells either by the spheroplast technique, described by Cregg et al., *Mol. Cell. Biol.* 5, 3376 (1985) [see also U.S. Pat. No. 4,879,231] or by the whole-cell lithium chloride yeast transformation system [Ito et al., *Agric. Biol. Chem.* 48. 341 (1984)], with modification necessary for adaptation to methylotrophic yeast, such as *P. pastoris* [See European Patent Application No. 312,934]. The whole-cell lithium chloride method is frequently more convenient in that it does not require the generation and maintenance of spheroplasts.

Positive transformants are characterized by Southern blot analysis [Maniatis et al., *Molecular Cloning: A Laboratory Manual*, Cold Spring Harbor Laboratory Press, Cold Spring Harbor, N.Y., U.S.A. (1982)] for the site of DNA integration; Northern blots Maniatis, Op. Cit., R. S. Zitomer and B. D. Hall, *J. Biol. Chem,* 251, 6320 (1976)] for methanol-responsive AAT gene expression; and product analysis for the presence of secreted AAT peptides in the growth media.

Transformed strains, which are of the desired phenotype and genotype, are grown in fermentors. For the large-scale production of recombinant DNA-based products in methylotrophic yeast, a three-stage, high cell-density, batch fermentation system is normally the preferred fermentation protocol employed. In the first, or growth stage, expression hosts are cultured in defined minimal medium with an excess of a non-inducing carbon source (e.g., glycerol). When grown on such carbon sources, heterologous gene expression is completely repressed, which allows the generation of cell mass in the absence of heterologous protein expression. Next, a short period of carbon source limitation growth is allowed. Subsequent to the period of growth under limiting conditions, methanol alone (referred to herein as "methanol excess fed-batch mode") or a limiting amount of a non-inducing carbon source plus methanol (referred to herein as "mixed-feed fed-batch mode") are added in the fermentor, inducing the expression of the APR gene driven by a methanol responsive promoter. This third stage is the so-called production stage.

The term "culture" means a propagation of cells in a medium conducive to their growth, and all subcultures thereof. The term "subculture" refers to a culture of cells grown form cells of another culture (source culture), or any subculture of the source culture, regardless of the number of subculturings which have been performed between the subculture of interest and the source culture.

According to a preferred embodiment of the present invention, the heterologous protein expression system used for AAT production utilizes the promoter derived from the methanol-regulated AOX1 gene of *P. pastoris*, which is very efficiently expressed and tightly regulated. This gene can be the source of the transcription terminator as well. The presently preferred expression cassette comprises, operationally associated with one another, the *P. pastoris* AOX1 promoter, DNA encoding the *S. cerevisae* AMF pre-pro sequence, a DNA sequence encoding mature AAT, and a transcription terminator derived from the *P. pastoris* AOX1 gene. Preferably, two or more of such expression cassettes are contained on one DNA fragment, in head-to-tail orientation, to yield multiple expression cassettes on a single contiguous DNA fragment. The presently preferred host cells to be transformed with multiple expression cassettes are *P. pastoris* cells having at least one mutation that can be complemented with a marker gene present on a transforming DNA fragment.

Vectors pPICZ A, B and C and pPICZα A, B and C and pGAPZ and pGAPZ alpha representing *P. pastoris* expression vectors can be obtained from Invitrogen Corporation, (San Deigo, Calif.). These vectors contain a unique Bg LII site 5' to the AOXL promoter and a unique Ba m HI site 3' to the *P. pastoris* transcription termination sequence to generate in vitro multimers for use in the invention.

The pPICZ alpha vectors do not contain a yeast origin of replication. Tranformants are therefore isolated if recombination occurs between the plasmid and the *Pichia* genome.

Kang et al describes in *Yeast,* 1998, Vol. 14, pages 371-381 a process for preparing alpha1-antitrypsin in *P. pastoris* with the strain GS115 at a pH of 3 in a shaker flask. However, it has now been found that a prolonged fermentation in order to obtain greater with any strain of *P. pastoris* results in a rapid degradation of alpha1-antitrypsin. Upscaling producing of GS115 and others occurred successfully at a pH between 5 and 6.8, preferably at 6 to 6.8.

It was further found that the shaker flask method of fermentation was detrimental to obtaining any significant yield. After 24 hours the biological activity of the protein was negligible either because of degradation or improper folding using a shaker flask method.

EXAMPLE 1

Alpha-1-Antitrypsin PCR Primers

Oligonucleotides are fully deprotected, desalted to remove organic contaminants, and delivered in TE Buffer, pH 8. The concentration is determined by multiplying the optical density at 260 nm by 33 μg/ml. The following is a description of each of the oligonucleotides synthesized as described in "*Pichia* Protocols" by Higgins et al, *Methods in Molecular Biology*, Vol. 103.

A. AntiTryp-FWD (32-mer with 20 bases complementary to starting template)

5' CTCGAG MG AGA GAG GAT CCC CAG GGA GAT GC 3'

Xho I lys arg -----antitrypsin (mature peptide)------->

MW=9957.3 D

Concentration=1 μg/μl

Total Yield=78.4 μg

B. AntiTryp-REV (a.k.a. AntiTryp 2: 32-mer with 24 bases complementary to starting template)

5' GCGGCCGC TTA TTT TTG GGT GGG ATT CAC CAC 3'

Not I stop <-------antitrypsin (mature peptide)---------

MW=9236.06 D

Concentration=0.284 μl/μl

Total Yield=71.0 μg

These primers were designed to allow subcloning into pPICA alpha and pGAPZalpha in frame with the alpha factor signal sequence utilizing Xho I and Not I sites. The AntiTryp Fwd primer includes the Xho I site followed by two codons (encoding Lysine and Arginine) that complete the Kex2 signal for cleavage, and the first 20 bases of the antitrypsin mature peptide. The AntiTryp Rev primer includes the Not I site followed by a stop codon and 21 bases of the antitrypsin mature peptide.

EXAMPLE 2

PcDNA3.1/GS-TOPO/alpha-1-Antitrypsin

Sequencing is produced by dye terminator cycle sequencing with AmpliTaq® using an ABI automated system. Products of the sequencing reaction are linearly amplified from small amounts of DNA template by thermal cycling of the annealing, extension, and denaturing steps of the reaction.

A. Sequencing Strategy:

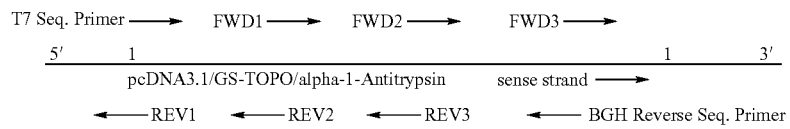

B. Sequence Analysis:

The sequencing gels are run overnight and the analysis is done by computer. The Chromatograms are reviewed in detail and any ambiguities are resolved with the help of Omiga and Sequencher sequence analysis software. The sequence of the primer is shown In Table 1:

TABLE 1

|  |  | Position | Tm | Length | SEQ ID NO |
|---|---|---|---|---|---|
| AntiTryp Fwd. 1: | CAGAAGACAGATACATCCCACCAT | 35 | 61.489 | 24 | 3 |
| AntiTryp Rev 1: | AGGATTTCATCGTGAGTGTCAG | 240 | 59.212 | 22 | 4 |
| AntiTryp Fwd 2: | TACTCAAGGGAAAATTGTGGATTT | 502 | 60.108 | 24 | 5 |
| AntiTryp Rev 2: | AGCTTCTTACAGTGCTGGATGTTA | 714 | 59.517 | 24 | 6 |
| AntiTryp Fwd 3: | GTTCAACAAACCCTTTGTCTTCTT | 1105 | 99.54 | 24 | 7 |
| AntiTryp Rev 3: | GGGAGACTTGGTATTTTGTTCAAT | 1156 | 59.670 | 24 | 8 |

EXAMPLE 3

Preparation of pGAPZalpha/alpha-1-Antitrypsin and pPI-CAalpha/alpha-1-antitrypsin A. Strategy:

The open reading frame (ORF) of interest, alpha-1-antitrypsin, was previously amplified using gene specific primers which would add an Xho I site and a Not I site to the ends of the PCR product. The product was TCR cloned into pcDNA3.1/GS-TOPO and five clones for each desired construct were sequenced to identify clones without any PCR induced mutations. The alpha-1-antitrypsin ORF was subcloned into pGAPZalpha and pPICZalpha at the Xho I and Not/sites for expression of each as an alpha factor fusion.

B. Method:

5 μg of pcDNA3.1/GS-TOPO/alpha-1-antitrypsin were digested with Xho I and Not I at 4 units of enzyme per μg of DNA for 1.5 hrs. at 37° C. 2 μg of pGAPZalpha and pPICZalpha were digested with Xho I and Not I at 4 units per μg 1.5 hrs. at 37° C. The digested samples were run on 0.8% PurElute agarose prep gels. DNA bands corresponding to the expected size for the antitrypsin insert (1204 bp) and the digested pGAPZalpha (3073 Kb) and pPICZalpha (3507 bp) were cut from the gels. DNA was recovered from the each of the gel slices using S.N.A.P.™ columns. The antitrypsin insert was prepared a second time in an identical fashion. Calf intestinal phosphatase (CIP) was utilized to dephosphorylate the 5' ends of the pGAPZalpha and pPICAalpha vector fragments. Ligations were performed with the prepared pGAPZalpha and pPICAalpha vector fragments and two preparations of alpha-1-antitrypsin insert at a ratio of ~2:1 (insert:vector). A ligation of each of the pGAPZalpha and pPICAalpha vector fragments alone were also performed to determine vector background. The reactions each contained 4 units of T4 DNA ligase and were incubated for 0.5 hrs at room temperature. These conditions were used in an attempt to decrease the vector:insert interactions (recombination events). The ligations were transformed into TOP10 cells and equal volumes were plated on LB agar/Zeo (50 μg/ml) plates.

The vector background [(#colonies on the vector alone plate I# colonies on the plus insert plates)×100] for each of the ligations and transformations was ≦0.4%. Ten colonies for each desired construct (5 with the first preparation of insert and 5 with the second) were screened by miniprep, restriction analysis and DNA sequencing.

Results

All clones contained an insert of the correct size and orientation for a pPICAalpha/alpha-1-antitrypsin or pGAPZalpha/alpha-1-antitrypsin positive clone. All clones for the pPICZalpha/alpha-1-antitrypsin were sequenced with both the antitrypsin Rev 1 and Rev 2 sequencing primers to confirm the sequence of the alpha fusion region and to screen for any vector:insert interactions that may have affected the DNA sequence of the insert. Clones for the pGADPDZalpha/alpha-1-antitrypsin were also sequenced with the antitrypsin Rev 1 and Rev 2 sequencing primers. Several clones for each construct contained an insertion of ~80 bp at the 5' end of the alpha-1-antitrypsin sequence, however, a few clones for each construct contained the expected sequence and these were the clones that were considered for continuation.

EXAMPLE 4

A. Strategy Fermentation Procedure:

One 5 liter fermentation of the *P. pastoris* clone SMD 1168H/pPICAα/α-1-antitrypsin was done at pH 5.0 and induced at a low wet cell weight to express the recombinant protein of interest. *Pichia pastoris* Hexametaphosphate Medium was used for the fermentation culture. The fed-batch fermentation was 4 days in duration achieving a final cell density of 447 g/l wet cell weight. Five 10 ml samples of the fermentation were collected to determine the culture's density. Supernatants of these samples were saved as fermentation time course samples. The fermentation was harvested by centrifugation after 72 hours of induction yielding 1890 ml of supernatant.

A similar run at pH 6.8 produced a greater cultural density which shows that pH was an important factor.

B. Batch Media:

Hexametaphosphate Medium: 25 g/l sodium hexametaphosphate (EM Science), 34 g/l Fermentation Basal Salts (Invitrogen), 9 g/l ammonium sulfate, 40 g/l glycerol, 4.35 ml/l PTM$_1$ trace metals (Invitrogen).

C. Fed-Batch Medium:

Glycerol Fed-batch: 50% (w/v) glycerol, 12 ml/l PTM$_1$ trace metals.

Methanol Fed-batch: 100% methanol, 12 ml/l PTM$_1$ trace metals.

D. Inoculum:

100 ul of glycerol stocks was inoculated into 40 ml of BMGY medium. This culture was grown 24 hours. The 40 ml culture was used to inoculate one flask containing 800 ml of the above batch medium. The fermenter was inoculated with this 200 ml of overnight shake flask culture. The remaining 600 ml was used to inoculate 3 other fermenters for the optimization experiment.

E. Fermenter Preparation:

The fermenter was sterilized with 2.25 liters containing the Fermentation Basal Salts, ammonium sulfate, and glycerol. Sodium hexametaphosphate and PTM$_1$ trace metals were made up as a 10× stock solution, filter sterilized, and added to the fermenter after it had been cooled to 30° C. The pH of the medium was adjusted to 5.0 with concentrated ammonium hydroxide for the initial batch culture.

The dO$_2$ pH probes were calibrated and checked for proper operation. Dissolved oxygen control was achieved by varying the agitation between 400 and 1000 rpm. When the agitation reached its maximum value, oxygen was supplemented into the air sparge automatically to maintain dO$_2$ setpoint. Control of pH was achieved by ammonium hydroxide addition. Foam control was achieved by automatic addition of KFO 673 antifoam (50% solution in methanol).

F. Fermentation:

Standard *Pichia pastoris* fermentation protocols were followed for the fermentation except that the pH was maintained between 5 and 6.8. After an initial batch phase growth on glycerol a glycerol fed-batch was started. The fermentation was fed 720 ml of 50% glycerol before induction. When the culture reached a wet cell weight of 351 g/L, the induction was initiated with methanol and PTM1 trace elements (12 mL/L) solution. If desired, the alpha 1-antitrypsin may be deglycosylated with Peptide: N-Glycosidase F.

EXAMPLE 5

The sequence encoding the alpha-1 Antitrypsin gene was successfully amplified from the phAT85 vector (obtained from ATCC; Manassas, Va.) by PCR. The PCR product was directly cloned into the PCR cloning vector pcDNA3.1/GS-TOPO using *E. coli* strain TOP10 as the host. Putative positive clones were analyzed by restriction analysis to verify the presence of a cloned insert and that the cloned insert contained the expected restriction sites originating from the PCR product ends (Xho I and Not I). pcDNA3.1/GS-TOPO does not contain Xho/and Not I sites; therefore, only PCR products cloned into the vector with correctly amplified termini will be subsequently excised by cutting with these enzymes.

EXAMPLE 6

The procedures of Example 4 and 5 were followed except that the strains of *P. pastoris* in each case were X33pGAP, X33pPIC, and SMD1168pGAP that produced biologically active alpha1-antitrypsin.

COMPARATIVE EXAMPLE

The procedure of Example 4 was followed except that the fermentation run was conducted at pH 3. After 24 hours a marked problem with the protein occurred during fermentation after 24 hours. After 7½ hours there was little or no level of biological activity noted. The results were configured by western blot and the dot-blot method utilizing the same antibodies and detection method used in the western blot.

COMPARATIVE EXAMPLE

Following the procedure of Example 4 except that a pH of 3.0 for the medium was utilized. This resulted in the production of cleavage products detected at lower molecular weight on western blots.

---

---

What is claimed is:

1. A method for producing a glycosylated biologically active alpha 1-antitrypsin polypeptide having the amino acid coding sequence of alpha 1-antitrypsin in the yeast *Pichia pastoris* in a fermentor, comprising the step of culturing a strain of said yeast selected from the group consisting of KM71 and SMD1168H, which strain comprises an expression cassette that contains a copy of a DNA sequence operably encoding said alpha 1-antitrypsin and operably associated with DNA encoding the yeast *Saccharomyces cerevisiae* alpha mating factor pre-pro sequence under the regulation of a promoter obtained from a methanol responsive gene of *Pichia pastoris* in a medium at a pH of about 6.8.

2. The method of claim 1 wherein the expression cassette includes in the direction of transcription a transcriptional terminator obtained from the *Pichia pastoris* gene.

3. The method of claim 1 wherein said strain is KM71.

4. The method of claim 1 wherein said strain is SMD1168H.

* * * * *